United States Patent [19]

Miller

[11] Patent Number: 4,538,012

[45] Date of Patent: * Aug. 27, 1985

[54] OLIGOMERIZATION OF LIQUID OLEFIN OVER A NICKEL-CONTAINING SILICACEOUS CRYSTALLINE MOLECULAR SIEVE

[75] Inventor: Stephen J. Miller, San Francisco, Calif.

[73] Assignee: Chevron Research Company, San Francisco, Calif.

[*] Notice: The portion of the term of this patent subsequent to Nov. 22, 2000 has been disclaimed.

[21] Appl. No.: 584,031

[22] Filed: Feb. 27, 1984

[51] Int. Cl.³ .............................................. C07C 2/02
[52] U.S. Cl. ..................................... 585/255; 585/533
[58] Field of Search ............................... 585/255, 533

[56] References Cited

U.S. PATENT DOCUMENTS 4,417,088 11/1983 Miller .................................. 585/533

*Primary Examiner*—Curtis R. Davis
*Attorney, Agent, or Firm*—S. R. La Paglia; W. K. Turner; V. J. Cavalieri

[57] ABSTRACT

A process for oligomerizing olefins in the liquid phase using nickel-containing silicaceous crystalline molecular sieve catalyst.

15 Claims, No Drawings

OLIGOMERIZATION OF LIQUID OLEFIN OVER A NICKEL-CONTAINING SILICACEOUS CRYSTALLINE MOLECULAR SIEVE

BACKGROUND OF THE INVENTION

1. Field of Invention

The present invention is in the field of olefin oligomerization. More specifically, the present invention relates to oligomerization of olefins in the liquid phase with a nickel-containing silicaceous crystalline molecular sieve catalyst.

2. Description of the Prior Art

Oligomerization and polymerization of olefins in the gas phase over various zeolites is known in the art. For example, U.S. Pat. No. 3,960,978 a process for producing a gasoline fraction containing predominantly olefinic compounds which comprises contacting a $C_2$ to $C_5$ olefin with a ZSM-5 type crystalline aluminosilicate zeolite at a temperature of from about 500° F. to about 900° F. as disclosed.

U.S. Pat. No. 4,021,501 describes the conversion of gaseous $C_2$ to $C_5$ olefins into gasoline blending stock by passage over ZSM-12 at temperatures of from about 400° F. to about 1200° F.

U.S. Pat. No. 4,211,640 discloses a process for the treatment of highly olefinic gasoline containing at least about 50% by weight of olefins by contacting said olefinic gasoline with crystalline aluminosilicate zeolites, such as those of the ZSM-5 type, so as to selectively react olefins other than ethylene and produce both gasoline and fuel oil.

U.S. Pat. No. 4,254,295 discloses a process for the oligomerization of olefins by contacting said olefins in the liquid phase with ZSM-12 catalyst at temperatures of 80° F. to 400° F.

U.S. Pat. No. 4,227,992 discloses a process for separating ethylene in admixture with light olefins by contacting said olefinic mixture with a ZSM-5 catalyst and thus producing both gasoline and fuel oil range materials.

The processes disclosed in these patents differ from that of the present invention in that they employ either a different catalyst, higher temperatures, or reaction in the gaseous phase.

Also, an important feature of several of the catalysts used in these prior art processes is that the catalyst must have reduced activity before oligomerization. Such catalyst of reduced activity may be obtained by steaming or by use in a previous conversion process.

This deactivation step is not required in the process of the present invention.

SUMMARY OF THE INVENTION

In accordance with the present invention, there has been discovered a process for oligomerizing alkenes comprising: (a) contacting a $C_2$ to $C_{20}$ olefin or mixture thereof in the liquid phase with a nickel-containing silicaceous crystalline molecular sieve in the hydrogen form selected from the group consisting of silicalite, an organosilicate disclosed in U.S. Pat. No. RE 29,948, CZM or mixtures thereof, at a temperature from about 45° F. to about 450° F.; (b) recovering an effluent comprising oligomerized alkene.

It has been found that the present process provides selective conversion of the olefin feed to oligomer products. The present process effects the conversion of the olefin feed to dimer, trimer, tetramer, etc., products with high selectivity. The product of the present reaction thus contains primarily olefin oligomer and little or no light cracked products, paraffins, etc.

The high selectivity is in part due to the surprisingly high oligomerization activity of the catalyst of the present process, which permits high conversion at low temperatures where cracking reactions are minimized.

The oligomers which are the products of the process of this invention are medium to heavy olefins which are highly useful for both fuels and chemicals. These include olefinic gasoline, such as from propylene dimerization, and extremely high quality midbarrel fuels, such as jet fuel. Higher molecular weight compounds can be used without further reaction as components of functional fluids such as lubricants, as viscosity index improvers in lubricants, as hydraulic fluids, as transmission fluids, and as insulating oils, e.g., in transformers to replace PCB containing oils. These olefins can also undergo chemical reactions to produce surfactants which in turn can be used as additives to improve the operating characteristics of the compositions to which they are added (e.g., lubricating oils) or can be used as primary surfactants in highly important activities such as enhanced oil recovery or as detergents. Among the most used surfactants prepared from the heavy olefins are alkyl sulfonates and alkyl aryl sulfonates.

A significant feature of the present process is the liquid phase contacting of the olefin feed and the nickel-containing silicaceous crystalline molecular sieves. There will be appreciated that the pressures and temperatures employed must be sufficient to maintain the system in the liquid phase. As is known to those in the art, the pressure will be a function of the number of carbon atoms of the feed olefin and the temperature.

The oligomerization process described herein may be carried out as a batch type, semi-continuous or continuous operation utilizing a fixed or moving bed catalyst system.

DESCRIPTION OF SPECIFIC EMBODIMENTS

The feeds used in the process of the invention contain alkenes which are liquids under the conditions in the oligomerization reaction zone. Under standard operating procedures it is normal both to know the chemical composition of feedstocks being introduced into a reaction zone and to set and control the temperature and pressure in the reaction zone. Once the chemical composition of a feedstock is known, the temperature and hydrocarbon partial pressures which will maintain all or part of the feed as liquids can be determined using standard tables or routine calculations. Conversely, once the desired temperature and pressure to be used in the reaction zone are set, it becomes a matter of routine to determine what feeds and feed components would or would not be liquids in the reactor. These calculations involve using critical temperatures and pressures. Critical temperatures and pressures for pure organic compounds can be found in standard reference works such as *CRC Handbook of Chemistry and Physics, International Critical Tables, Handbook of Tables for Applied Engineering Science,* and Kudchaker, Alani, and Zwolinski, Chemical Reviews 68, 659 (1968), all of which are incorporated herein by reference. The critical temperature for a pure compound is that temperature above which the compound cannot be liquefied regardless of pressure. The critical pressure is the vapor pressure of the pure compound at its critical temperature. These points for several pure alkenes are listed below:

|  | $T_c$ °C. | (°F.) | $P_c$-atm (bar) |
| --- | --- | --- | --- |
| ethene | 9.21 | (48.6) | 49.66 (50.3) |
| propene | 91.8 | (197.2) | 45.6 (46.2) |
| 1-butene | 146.4 | (295.5) | 39.7 (40.2) |
| 1-pentene | 191.59 | (376.9) | 40 (40.5) |
| iso-2-pentene | 203 | (397) | 36 (36.5) |
| 1-hexene | 230.83 | (447.49) | 30.8 (31.2) |
| 1-heptene | 264.08 | (507.34) | 27.8 (28.2) |
| 1-octene | 293.4 | (560.1) | 25.6 (25.9) |
| 1-decene | 342 | (648) | 22.4 (22.7) |

It can be appreciated that at temperatures above about 205° C. (401° F.), pure $C_5$ and lower alkenes must be gaseous, while pure $C_6$ and higher alkenes can still be liquefied by applying pressure. Similarly, above about 275° C. (527° F.) pure $C_8$ and higher alkenes can be maintained in the liquid state, while pure $C_7$ and lower alkenes must be gaseous.

Typical feeds are mixtures of compounds. But even so, once the chemical composition of the feed is known, the critical temperature and pressure of the mixture can be determined from the ratios of the chemicals and the critical points of the pure compounds. See for example, the methods of Kay and Edmister in *Perry's Chemical Engineers Handbook*, 4th Edition, pages 3-214, 3-215 (McGraw Hill, 1963), which is incorporated by reference.

Of course, the only constraint on the alkenes present in the feed and which are to react in the oligomerization reaction zone is that these alkenes be liquids under the conditions in the reaction zone (the conditions include a temperature of less than about 450° F.). The chemical composition of the alkenes can be varied to obtain any desired reaction mixture or produce mix, so long as at least some of the alkene components of the feed are liquid.

The alkene chains can be branched. And, even though the nickel-containing silicaceous crystalline molecular sieve catalysts used in this invention are intermediate pore size molecular sieves, alkenes having quaternary carbons (two branches on the same carbon atom) can be used. But where quaternary carbons are present, it is preferred that the branches are methyl.

The preferred alkenes are straight chain, or n-alkenes, and the preferred n-alkenes are 1-alkenes. The alkenes have from 2 to 20 carbon atoms, and more preferably have from about 2 to about 6 carbon atoms.

One of the surprising discoveries of this invention is that under certain reaction conditions, longer chain alkenes can be polymerized instead of being cracked to short chain compounds. Additionally, the oligomers produced from long n-1-alkenes are very highly desirable for use as lubricants. The oligomers have surprisingly little branching so they have very high viscosity indices, yet they have enough branching to have very low pour points.

The feed alkenes can be prepared from any source by standard methods. Sources of such olefins can include FCC offgas, coker offgas, syngas (by use of CO reduction catalysts), low pressure, nonhydrogenative zeolite dewaxing, alkanols (using high silica zeolites), and dewaxing with crystalline silica polymorphs. Highly suitable n-1-alkene feeds, especially for preparing lubricating oil basestocks, can be obtained by thermal cracking of hydrocarbonaceous compositions which contain normal paraffins or by Ziegler polymerization of ethene.

Often, suitable feeds are prepared from lower alkenes which themselves are polymerized. Such feeds including polymer gasoline from bulk $H_3PO_4$ polymerization, and propylene dimer, and other olefinic polymers in the $C_4$-$C_{20}$ range prepared by processes known to the art.

The nickel-containing silicaceous crystalline molecular sieves used in this invention are of intermediate pore size. By "intermediate pore size", as used herein, is meant an effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as faujasites and mordenites, they can differentiate between n-alkanes and slightly branched alkanes on the one hand and larger branched alkanes having, for example, quaternary carbon atoms.

The effective pore size of the molecular sieves can be measured using standard adsorption techniques and hydrocarbonaceous compounds of known minimum kinetic diameters. See Breck, *Zeolite Molecular Sieves*, 1974 (especially Chapter 8) and Anderson et al, J. Catalysis 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.8). Compound having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms.

In performing adsorption measurements to determine pore size, standard techniques are used. It is convenient to consider a particular molecule as excluded if it does not reach at least 95% of its equilibrium adsorption value on the zeolite in less than about 10 minutes (p/po=0.5; 25° C.).

Silicalite is disclosed in U.S. Pat. No. 4,061,724; the "RE 29,948 organosilicates" are disclosed in U.S. Pat. No. RE 29,948; chromia silicates, CZM, are disclosed in Ser. No. 450,419, Miller, filed Dec. 16, 1982. These patents are incorporated herein by reference.

The crystalline silica polymorphs, silicalite, and U.S. Pat. No. RE 29,948 organosilicates, and the chromia silicate, CZM are essentially alumina free.

"Essentially alumina free", as used herein, is meant the product silica polymorph (or essentially alumina-free silicaceous crystalline molecular sieve) has a silica:alumina mole ratio of greater than 200:1, preferably greater than 500:1. The term "essentially alumina free" is used because it is difficult to prepare completely aluminum free reaction mixtures for synthesizing these materials. Especially when commercial silica sources are used, aluminum is almost always present to a greater or lesser degree. The hydrothermal reaction mixtures from which the essentially alumina free crystalline silicaceous molecular sieves are prepared can also be referred to as being substantially aluminum free. By this usage is meant that no aluminum is intentionally added to the reaction mixture, e.g., as an alumina or aluminate reagent, and that to the extent aluminum is present, it occurs only as a contaminant in the reagents.

The most preferred molecular sieve is the zeolite Ni-silicalite. Of course, these and the other molecular sieves can be used in physical admixtures.

When synthesized in the alkali metal form, the zeolites may be conveniently converted to the hydrogen form by well known ion exchange reactions, for example, by intermediate formation of the ammonium form as a result of ammonium ion exchange and calcination of the ammonium form to yield the hydrogen form or by treatment with dilute acid such as hydrochloric acid.

Nickel is incorporated into these silicaceous crystalline molecular sieves according to techniques well known in the art such as impregnation and cation exchange. For example, typical ion exchange techniques would be to contact the particular sieve in the hydrogen form with an aqueous solution of a nickel salt. Although a wide variety of salts can be employed, a particular preference is given to chlorides, nitrates and sulfates. The amount of nickel in the zeolites range from 0.5% to 10% by weight and preferably from 1% to 5% by weight.

Representative ion exchange techniques are disclosed in a wide variety of patents including U.S. Pat. Nos. 3,140,249; 3,140,251; 3,960,978, 3,140,253 and 4,061,724.

Following contact with the salt solution, the zeolites are preferably washed with water and dried at a temperature ranging from 150° F. to about 500° F. and thereafter heated in air at temperatures ranging from about 500° F. to 1000° F. for periods of time ranging from 1 to 48 hours or more.

The nickel-containing silicaceous crystalline molecular sieve catalysts can be made substantially more stable for oligomerization by including from about 0.2% to 3% by weight and preferably 0.5% to 2% by weight of the Group IIB metals, zinc or cadmium and preferaby zinc. A primary characteristic of these substituents is that they are weak bases, and are not easily reduced. These metals can be incorporated into the catalysts using standard impregnation, ion exchange, etc., techniques. Strongly basic metals such as the alkali metals are unsatisfactory as they poison substantially all of the polymerization sites on the zeolite. For this reason, the alkali metal content of the zeolite is less than 1%, preferably less than 0.1%, and most preferably less than 0.01%. The feed should be low in water, i.e., less than 100 ppm, more preferably less than 10 ppm, in sulfur, i.e., less than 100 ppm and preferably less than 10 ppm, in diolefins, i.e., less than 0.5%, preferably less than 0.05% and most preferably less than 0.01%, and especially in nitrogen, i.e., less than 5 ppm, preferably less than 1 ppm and most preferably less than 0.2 ppm.

The polymerization processes of the present invention are surprisingly more efficient with small crystallite sieve particles than with larger crystalline particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The molecular sieves can be composited with inorganic matrix materials, or they can be used with an organic binder. It is preferred to use an inorganic matrix since the molecular sieves, because of their large internal pore volumes, tend to be fragile, and to be subject to physical collapse and attrition during normal loading and unloading of the reaction zones as well as during the oligomerization processes. Where an inorganic matrix is used, it is highly preferred that the matrix be substantially free of hydrocarbon conversion activity. It can be appreciated that if an inorganic matrix having hydrogen transfer activity is used, a significant portion of the oligomers which are produced by the molecular sieve may be converted to paraffins and aromatics and to a large degree the benefits of my invention will be lost.

The reaction conditions under which the oligomerization reactions take place include hydrocarbon partial pressures sufficient to maintain the desired alkene reactants in the liquid state in the reaction zone. Of course, the larger the alkene molecules, the lower the pressure required to maintain the liquid state at a given temperature. As described above, the operating pressure is intimately related to the chemical composition of the feed, but can be readily determined. Thus, the required hydrocarbon partial pressure can range from 31 bar at 450° F. for a pure n-l-hexene feed to about atmospheric pressure for a n-l-$C_{15}$-$C_{20}$ alkene mixture. In the process of this invention, both reactant and product are liquids under the conditions in the reaction zone, thus leading to a relatively high residence time of each molecule in the catalyst.

The reaction zone is typically operated below about 450° F. Above that temperature not only significant cracking of reactants and loss of oligomer product take place, but also significant hydrogen transfer reactions causing loss of olefinic oligomers to paraffins and aromatics take place. An oligomerization temperature in the range from about 90° F. to 350° F. is preferred. Liquid hourly space velocities can range from 0.05 to 20, preferably from 0.1 to about 4.

Once the effluent from the oligomerization reaction zone is recovered, a number of further processing steps can be performed.

If it is desired to use the long chain compounds which have been formed in middle distillate fuel such as jet of diesel or in the lube oils as base stock, the alkene oligomers are preferably hydrogenated.

All or part of the effluent can be contacted with the molecular sieve catalyst in further reaction zones to further react unreacted alkenes and alkene oligomers with themselves and each other to form still longer chain materials. Of course, the longer the carbon chain, the more susceptible the compound is to being cracked. Therefore, where successive oligomerization zones are used, the conditions in each zone must not be so severe as to crack the oligomers. Operating with oligomerization zones in series can also make process control of the exothermic oligomerization reactions much easier.

One particularly desirable method of operation is to separate unreacted alkenes present in the effluent from the alkene oligomers present in the effluent and then to recycle the unreacted alkenes back into the feed.

The following examples further illustrate this invention.

EXAMPLES

Example 1

A Zn-silicalite catalyst was prepared in the following manner. H-silicalite of 240 $SiO_2/Al_2O_3$ mole ratio was mixed with peptized and neutralized Catapal alumina at a 67/33 sieve/alumina weight ratio, extruded through a 1/16" die, dried overnight at 300° F. under $N_2$, then calcined in air for 8 hours at 850° F. The catalyst was impregnated by the pore-fill method to 1 weight % Zn using an aqueous solution of $Zn(NO_3)_2$, then dried and calcined as done previously.

Example 2

The catalyst of Example 1 was impregnated to 3 weight % Ni by the pore-fill method using an aqueous solution of $Ni(NO_3)_2.6H_2O$. The catalyst was dried overnight under $N_2$ at 300° F., then calcined in air for 8 hours at 850° F.

Example 3

The Zn-silicalite catalyst of Example 1 was tested for converting propylene to higher molecular weight products at 150° F., 1000 psig, and 0.5 LHSV. At 24 hours onstream, conversion to $C_5+$ was 3.2% with 38% selectivity to dimer.

Example 4

The Ni-Zn-silicalite catalyst of Example 2 was tested for converting propylene at the same conditions as in Example 3. At 40 hours onstream, conversion to $C_5+$ was 72.7% with 77% selectivity to dimer.

What is claimed is:

1. A process for oligomerizing alkenes comprising:
   (a) contacting a $C_2$ to $C_{20}$ olefin or mixture thereof in the liquid phase with a nickel-containing silicaceous crystalline molecular sieve in the hydrogen form selected from the group consisting of silicalite, an organosilicate disclosed in U.S. Pat. No. RE 29,948, and CZM or mixtures thereof, at a temperature from about 45° F. to about 450° F.;
   (b) recovering an effluent comprising oligomerized alkene.

2. The process of claim 1 wherein the nickel-containing silicaceous crystalline molecular sieve also contains zinc cation.

3. The process of claim 1 wherein said contacting is carried out at a LHSV of from about 0.2 to 5.

4. The process of claim 1 wherein the pressure is from about 50 to about 1600 psig.

5. The process of claim 1 wherein said nickel-containing silicaceous crystalline molecular sieve is silicalite.

6. The process of claim 1 wherein said nickel-containing silicaceous crystalline molecular sieve is organosilicate disclosed in U.S. Pat. No. RE 29,948.

7. The process of claim 1 wherein said nickel-containing silicaceous crystalline molecular sieve is CZM.

8. The process of claim 5 wherein the nickel-containing silicaceous crystalline molecular sieve also contains zinc cation.

9. The process of claim 6 wherein the nickel-containing silicaceous crystalline molecular sieve also contains zinc cation.

10. The process of claim 7 wherein said nickel-containing silicaceous crystalline molecular sieve also contains zinc cation.

11. The process of claim 1 wherein said alkenes comprise n-alkenes.

12. The process of claim 15 wherein said n-alkenes are 1-alkenes.

13. The process of claim 1 wherein said alkenes comprise branched chain alkenes and wherein the branches of said branched chain alkenes are methyl branches.

14. The process of claim 1 further comprising the step of hydrogenating said alkene oligomers.

15. The process of claim 1 further comprising the steps of: separating unreacted alkenes present in said effluent from alkene oligomers present in said effluent and recycling said unreacted alkenes into the feed for said contacting step.

* * * * *

UNITED STATES PATENT AND TRADEMARK OFFICE
CERTIFICATE OF CORRECTION

PATENT NO. : 4,538,012
DATED : August 27, 1985
INVENTOR(S) : Stephen J. Miller

It is certified that error appears in the above–identified patent and that said Letters Patent are hereby corrected as shown below:

Col. 1, line 21, "as disclosed" should read --is disclosed--.

Col. 1, line 22, "4,021,501" should read --4,021,502--.

Col. 4, lines 33-34, "benzene (5.8)" should read
--benzene (5.85), and toluene (5.8).--

Col. 6, line 51, "jet of diesel" should read --jet or diesel--.

Signed and Sealed this

Eighteenth Day of February 1986

[SEAL]

Attest:

DONALD J. QUIGG

Attesting Officer     Commissioner of Patents and Trademarks